United States Patent [19]

Mau-Tung et al.

[11] 4,328,701

[45] May 11, 1982

[54] APPARATUS FOR DETERMINING THE BEHAVIOR OF A LIQUID DURING COAGULATION AND THE LIKE

[75] Inventors: Do Mau-Tung; Do M. Lam, both of Velizy, France

[73] Assignee: Societe Probio DMS, France

[21] Appl. No.: 143,750

[22] Filed: Apr. 25, 1980

[30] Foreign Application Priority Data

Apr. 27, 1979 [FR] France .................................. 79 10915

[51] Int. Cl.³ ....................... G01N 11/10; G01N 33/48
[52] U.S. Cl. .......................................... 73/59; 73/64.1
[58] Field of Search ................................... 73/59, 64.1

[56] References Cited

U.S. PATENT DOCUMENTS

| | | | |
|---|---|---|---|
| 2,550,052 | 4/1951 | Fay | 73/59 |
| 2,814,945 | 12/1957 | Michaux et al. | 73/59 |
| 3,714,815 | 2/1973 | Hartert | 73/59 X |
| 4,045,999 | 9/1977 | Palmer | 73/59 |
| 4,148,216 | 4/1979 | Do et al. | 73/59 |
| 4,193,293 | 3/1980 | Cavallari | 73/64.1 |

FOREIGN PATENT DOCUMENTS 1558516  1/1969  France ................................. 73/64.1

*Primary Examiner*—Gerald Goldberg
*Assistant Examiner*—Joseph W. Roskos
*Attorney, Agent, or Firm*—Larson and Taylor

[57] ABSTRACT

An apparatus for measuring or observing parameters representative of the coagulation and/or the lysis of a coagulable liquid, such as blood, comprises a torsion thread, a driving body supported by the torsion thread to be dipped in the liquid, a vessel containing the liquid is oscillated with a predetermined angular amplitude and period around an axis substantially identical with the torsion thread.

Detection means comprise an inductor driven by the thread and a fixed position-detector which delivers an electrical signal representative of the amplitude of the oscillations of the torsion thread.

The torsion thread is constituted by a wire stretched between two anchoring points and bearing the mass.

9 Claims, 6 Drawing Figures

APPARATUS FOR DETERMINING THE BEHAVIOR OF A LIQUID DURING COAGULATION AND THE LIKE

BACKGROUND AND SUMMARY OF THE INVENTION

The invention relates to an apparatus for measuring parameters representative of the coagulation or of the lysis of a coagulable liquid.

A prior art apparatus of that type comprises a torsion member; a driving body supported by the torsion member for immersion in the liquid; means for oscillating a vessel containing the liquid with a predetermined angular amplitude and period around an axis substantially identical with that of the torsion member; means for detecting the amplitude of the torsion of said member, said detection means comprising an inductor element movable as a function of the torsion of said member and fixed position detector means, operating by induction, adapted to cooperate with the movable inductor element, so that said detector means deliver an electrical signal representing the amplitude of the oscillations of said torsion member. U.S. Pat. No. 4,148,216 discloses a particular embodiment of such an apparatus in which the driving body is suspended on the torsion member constituted by a thread or ribbon. For the device to operate satisfactorily, inclination of the work table to the horizontal should be avoided.

It is an object of the invention to provide an improved device which can operate satisfactorily without requiring accurate adjustment of horizontality; it is another object to provide a device which may operate without means damping transverse oscillations.

It is still another object to improve the capability of the device to accept rough treatment and forces arising from transportation and handling. A device of the above defined type according to the invention has a torsion member constituted by a thread stretched between two anchoring points and bearing said body, the points being placed approximately vertically over one another during operation.

The term "thread" must be construed in a broad sense and as covering notably the case where thread includes several pieces connected by a rigid element.

The body is typically fixed removably at the lower end of a yoke surrounding one of the anchoring points (typically the lower anchoring point) and bearing the inductor element at its upper part.

The yoke may form a rotary unit with a disk centered on the thread and lockable in position by a locking mechanism.

Other features and improvements of the invention will appear from the following description of a particular embodiment, given by way of example.

SHORT DESCRIPTION OF THE DRAWINGS

DETAILED DESCRIPTION OF A PREFERRED EMBODIMENT

Figure 1:
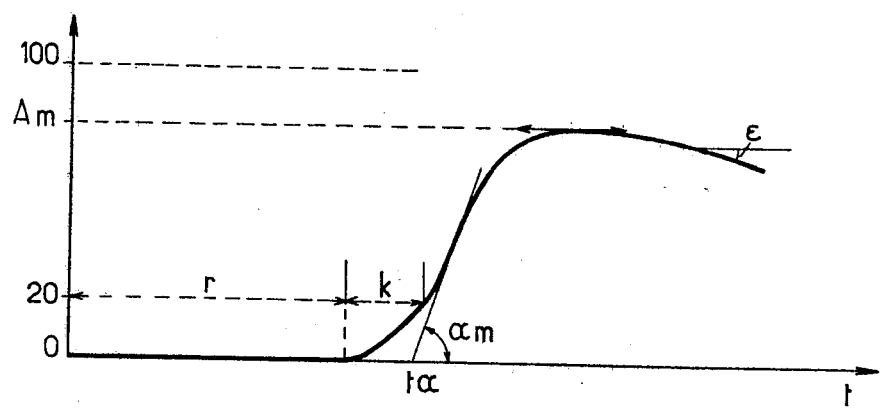
FIG. 1 is an example of a thromboelastogram that is a curve representing the variation as a function of time of the amplitude of the angular oscillations of the body of a measuring device when the vessel containing the liquid studied, is oscillated at constant frequency and amplitude.

Before the invention is described, some important features of a thromboelastogram will be recalled with reference to FIG. 1.

In FIG. 1 there are indicated:

the maximum amplitude Am (which can be expressed in the form of a ratio from 0 to 100% of the angular amplitude of oscillations impressed to the vessel containing the product under study), the time period r at the end of which an oscillation of a body dipping into the product under study is initially detected, the time period k, starting from the expiration of r, at the end of which the value of the oscillation has reached 20% of the amplitude of the oscillation of the vessel;

the maximum value of tan $\alpha_m$ of the slope of the curve;

the abscissa $t\alpha$ corresponding to the tangent of maximum slope;

the slope tan $\epsilon$ of the decreasing portion of the thromboelastogram.

In a sophisticated version of the apparatus which will now be described, all above data can be computed and displayed, which considerably simplifies the exploitation thereof.

The apparatus comprises a frame (not shown), provided with two vertical columns 10. A support 11 and a carriage 12 are slidably mounted on the columns. The support 11, shown in FIG. 2 as a U-shaped member whose arms are connected by a connecting rod 13 will in practice consist of several assembled parts. In the embodiment shown in FIG. 3, it includes two horizontal plates 14 and 15 connected by rod 13 and by two symetrical props 16. Plates 14 and 15 are formed with openings located rearwardly of props 16, whose diameter corresponds to that of the column 10.

Support 11 bears the oscillating unit of the device. That unit comprises a yoke 17 whose lower point is provided with a fastening tip 18 for removable connection of the body 19 arranged to dip into the coagulable product to be studied. Yoke 17 straddles the front end portion of the lower plate 15. Its upper portion is provided with a locking disk 20 whose function will be indicated below and is extended by a narrow flat bar 21. The upper end of this bar is secured to a horizontal arm 22 bearing an inductor element 23, typically a ferrite core, forming the movable element of the detector means. A counterweight 24 is adjustable in position on the arm 22 for balancing the latter.

The movable unit is carried by a thread 25 stretched between two anchoring points on the upper and lower plates 14,15. Due to the presence of the yoke 17, it is possible to place the driving mass 19 below the lower plate 15, hence to dip it in the vessel containing the coagulable product studied.

Figure 3:
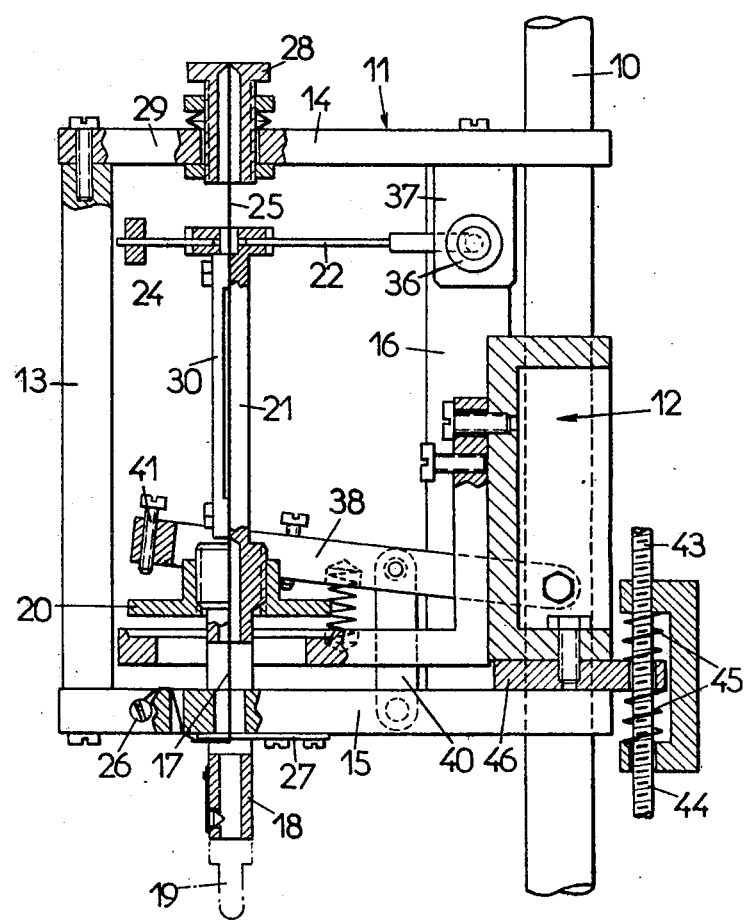
FIG. 3 shows the mechanical members of an apparatus corresponding to the diagram of FIG. 2, in section along a plane passing through the suspension thread.

The anchoring points can be as shown in FIG. 3. The thread 25 is fixed on the lower plate 15 by a screw 26, projects downwardly through the plate and passes back upwardly through tray 15, at a position determined accurately by a centering plate 27. The top end of the thread 25 is fixed to a threaded bush 28 held on the tray 14 in a position axially adjustable by means of two nuts 29 for adjustment of the tensile force.

Numerous methods of fastening the rotary mechanism to the thread may be used. In the embodiment shown in FIG. 3, the thread is squeezed between the bar 21 and a removable cover sheet.

As already indicated, the continuous thread may be substituted with several successive portions connected by the movable unit.

The device further includes means for imparting oscillations on a vessel containing the coagulable liquid about an axis substantially along thread 25. The means will not be described in detail since they can be identical with those mentioned in U.S. Pat. No. 4,148,216.

Referring to FIG. 1 the means comprise a support 31 for the vessel containing the liquid, provided with an arm 32 oscillating around a vertical axis under the action of a cam 33 rotated by an electric motor 34. A spring 35 holds the arm in contact with cam 33.

The support 11 further carries the fixed portion of the position detector means; in the illustrated embodiment it comprises two coils 36 placed on a dowel 37 fixed to plate 14. An electric motor (not shown) may be provided to lower the chassis until body 19 dips into the vessel and to lift it.

Figure 2:
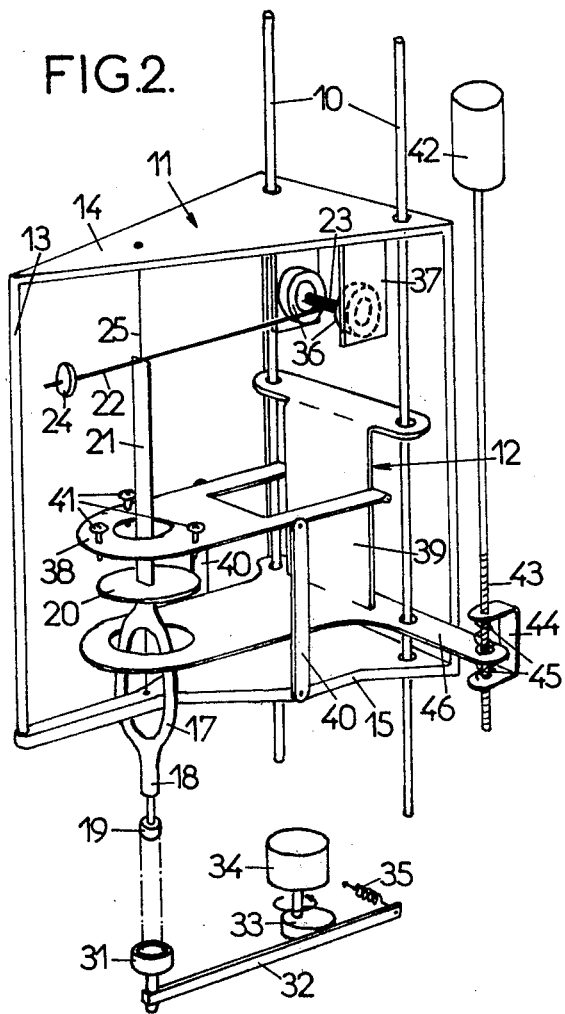
FIG. 2 is a schematic isometric view of the essential mechanical parts of the apparatus.

The apparatus includes a mechanism for locking the movable unit both against vertical movement and rotational movement and enables the assembly to take shocks and handling without damage. The locking mechanism includes the carriage 12 and a tray 38. The tray is mounted on a vertical upright 39 of the carriage 12 for oscillating movement around an axis perpendicular to thread 25. Two link rods 40 constitute between the tray 38 and the lower tray 15, a linkage hinged around two axis parallel to the rocking axis of the tray 38 on the upright 39. Thus, when carriage 12 is moved upwards from the position in which it is shown in FIG. 2, the tray 38 rocks downwardly. Disk 20 can thus be squeezed between a lower pallet belonging to carriage 12 and adjustment screws 41 borne by tray 38. Conversely, if the carriage 12 is moved down with respect to support 11, the tray 38 and the pallet spread apart symetrically and release disk 20.

The movements of the carriage 39 are controlled by a mechanism provided to avoid application of excess forces. It includes a reversible electric motor 42 (FIGS. 2 and 3) whose housing is fastened to support 11. This motor, whose direction of rotation depends on the polarity which is applied to it, drives a threaded rod 43 screwed into a yoke or bracket 44 fixed against rotation. Energization of the motor causes the yoke 44 to move up or down, depending on the direction of rotation of the motor. A resilient centering device, consisting of two springs in the embodiment illustrated in FIGS. 2 and 3, tends to maintain a tab 46 of carriage 12 in the middle of the yoke 44. Thus, when the carriage 12 comes into upper or lower abutment against the support, the application of excessive forces to the motor 42 is avoided by compression of the corresponding spring 45.

Figure 4:
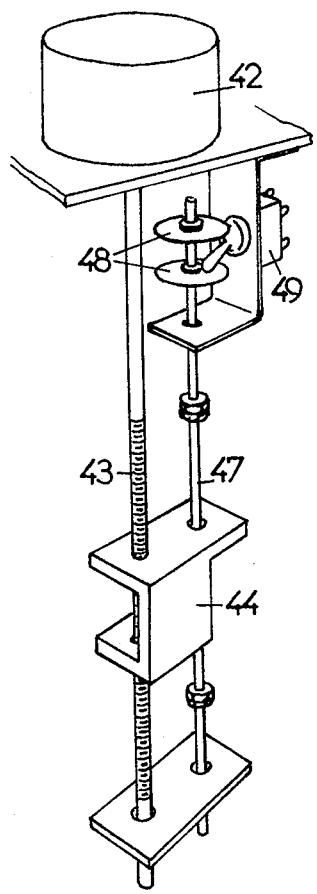
FIG. 4 is an isometric schematic view of the driving mechanism of the carriage of the apparatus of FIG. 2.
Figure 5:
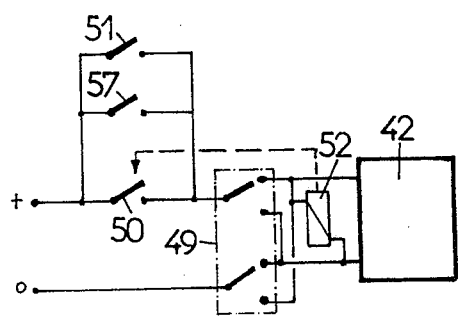
FIG. 5 is an electrical diagram of part of the electric circuit of the device.

The apparatus typically includes a single control for up and down movement for avoiding errors. This requires a circuit which is responsive to arrival of the motor in end position and then causes the next movement to occur in the reverse direction. In the embodiment shown in FIG. 4, a rod 47 secured to the lug 46 (and, in addition, retaining the bracket 44 against rotation) bears two washers 48 actuating an inverting switch 49. Switch 49 may be connected as indicated in FIG. 5. The electric supply circuit of motor 42 includes the movable contact 50 of a nonpolarized relay, in parallel relation with a manual control switch 51, and the inverting switch 49. The coil 52 of the relay is placed directly across the terminals of the motor. Closing of the switch 51 causes the supply of the motor with a polarity determined by switch 49. As soon as supply is effected, the contact 50 comes into working position and the switch 51—which can be a push-button—may be released.

Motor 42 drives the carriage as far as its stop position, for which the switch 49 is reversed. This reversal causes a brief cut-off which de-energized the relay and contact 50 opens. A further action on the switch 51 will cause the movement of the motor 42 in the direction contrary to the preceding one.

Figure 6:
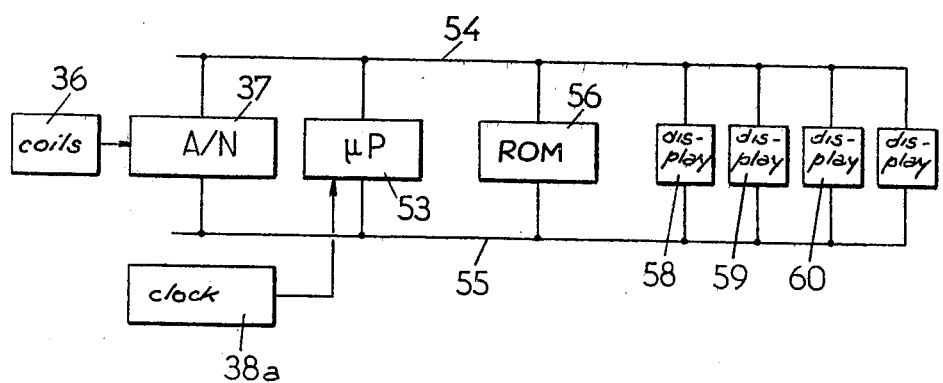
FIG. 6 is a block diagram, showing how the apparatus may be controlled by a microprocessor and the results may be displayed.

The control of the system and the calculations can be effected by electronic means so as to provide the user with immediately readable results. A block diagram of such means is given in FIG. 6, and is digitally implemented. The assembly includes a microprocessor 53 (for example SC/MP available from NATIONAL SEMICONDUCTOR, 80-82 from INTEL or 6800 from MOTOROLA) connected to address bus 54 and data bus 55. Read-only memories or ROM 56 containing the application programs may be connected to buses 54 and 55. The output signal supplied by the fixed position-detector means 36 is digitized in an A/D converter 37 and applied to the microprocessor, provided with an external clock 38a. The assembly also includes display units whose number and function will depend on the number of parameters or data which it is desired to display simultaneously or successively.

The device will also include call buttons for displaying selected parameters or data. The program will be written to compute from data provided by the sensor 36, the amplitude A in digital form and those of parameters Am, r, k, tan, αm, td and ε which it is desired to have available. Amplitude A will typically be continuously computed while the other data will be stored in a RAM.

A sequence starting button may be provided. The microprocessor will then deal with the sequence of steps, and notably control the operation of the motor by means of an additional switch 57 (FIG. 5).

In practice, it will often be useful to provide several display devices enabling the indications below to be supplied.

A first display window 58, of large size, will continuously display the time t from the start of the measurement sequence until the latter is terminated. A second window 59 displays the amplitude A of the oscillations in the course of the measurements. A third window 60 displays the parameter r when it has become available.

The microprocessor may be programmed to carry out the following sequence of operations, in response to actuation of a single start push button:

the support being initially in its upper position, the micro-processor causes it to move down, at constant speed, until the body is in the measuring tank, and then stops the motor;

once the body is in position, the measurement is started automatically, the apparatus stops automatically as soon as the thromboelastogram exhibits a uniform descending slope tan ϵ; the support is then moved up automatically to its upper rest position and, at the same time, a visual or audible signal indicating end of the measurement is delivered: it may consist of the display of the word "end" in the measuring window 58, if, for any reason, it is desired to stop a measurement under way, it suffices to press the button to raise the support up to its upper rest position, while the measuring process is reset to zero, at the end of the measurement, permanent display of the maximum amplitude Am may be provided in the window 58 while the other parameters appear in the other windows, on call by means of particular buttons.

The possibility of displaying any one of several predetermined parameters in the same display window 58 represents an important factor of economy and convenience, especially on an apparatus whose housing is of small size.

A convenient solution for effecting a display devoid of ambiguity consists of providing, on the housing of the apparatus, control buttons equal in number to that of the parameters or data to be displayed in the window 58, each button being identified, on the one hand, by a reference numeral and, on the other hand, by an inscription in plain language. The electronic circuit associated with the window is then provided to display the number of the button indicating the parameter displayed in the left-hand part of the window, and the digital value of the parameter at the right.

This method of display can be effected simply in an apparatus including a microprocessor. It suffices to provide an address for each of the control-buttons and to program the microprocessor so that it determines, the condition of the buttons at regular intervals. This interrogation is effected by emitting on the address bus a call code which is transmitted to the group of buttons by an interrogation line. If a button has been actuated, it is identified by a comparator associated with the button which enables a gate for transmission to the data bus of a number that the computer decodes as the address of a computed parameter in the RAM memory. The value of the parameter is then transmitted to the display circuit associated with the window. Holding circuits may be provided so that the number remains displayed until the other button is actuated.

We claim:

1. Apparatus for determining the viscous behaviour of a liquid during coagulation and lysis thereof and the like, including:

support means, vertical torsion means stretched between an upper anchoring point and a lower anchoring point on said support means, an oscillatory body located below the lower anchoring point and suspended to said vertical torsion means, whereby said torsion means tend to return said body to a predetermined angular position about the axis of the torsion means, means for supporting a vessel for said liquid and for imparting to said vessel an oscillatory movement of predetermined frequency and amplitude substantially about said axis, and amplitude measuring means for measuring the amplitude of the oscillations of said body when immersed in said liquid, said amplitude measuring means comprising electrical induction means having a movable element operatively connected to said body for oscillatory movement therewith and a stationary element having output terminal means of a type which delivers, on said terminal means, an electrical signal whose amplitude is representative of the amplitude of the oscillatory movements of said body and further comprising electrical means for measuring the amplitude of said electrical signal.

2. Apparatus according to claim 1, further comprising a yoke straddling said lower anchoring point, secured to said torsion means, having its lower end portion connectable to said body and carrying said movable element.

3. Apparatus according to claim 2, wherein the yoke forms a rotary unit with a disk centered on the thread and lockable in position by a locking mechanism.

4. Device according to claim 3, further including a support having a lower arm traversing the yoke and an upper arm, said anchoring points being provided on said arms and including means for moving said support vertically to dip said body into the vessel and withdrawing it therefrom.

5. Apparatus according to claim 4 wherein the locking mechanism comprises a carriage provided with means for moving it parallel to the torsion means with respect to said support, towards the disk and from the disk, and a tray hinged to the carriage and to the support whereby the disk is clamped symetrically by the carriage and the tray on movement of the carriage towards the disk.

6. Apparatus according to claim 5, wherein the locking mechanism comprises a motor for driving the carriage with respect to the chassis, through resilient force-limiting centering means.

7. Apparatus according to claim 6, wherein the resilient centering means is operatively associated with a switch reversing the polarity of an electric supply of the motor and cutting off said supply when said resilient centering device comes into abutment against stop means.

8. Apparatus according to claim 1, further including computing and display means, for providing one at least of the maximum amplitude of the oscillations, the time at the end of which an oscillation is detected, the maximum value of the rising slop of the curve representing amplitude as a function of time, and the maximum slope.

9. Apparatus according to claim 8, wherein the display means comprise a display window and operator-controlled selector means, for causing display of any one of parameters stored in a memory of the computing means in the window.

\* \* \* \* \*